US012776106B2

(12) United States Patent
Demanget

(10) Patent No.: US 12,776,106 B2
(45) Date of Patent: Oct. 27, 2026

(54) AUGMENTED REALITY (AR) VIRTUAL OBJECTS FOR ALIGNING AN INSTRUMENT PLANE WITH A PLANNED TARGET PLANE

(71) Applicant: DePuy Ireland Unlimited Company, Ringaskiddy (IE)

(72) Inventor: Nicolas Demanget, Saint-Egrève (FR)

(73) Assignee: DePuy Ireland Unlimited Company, Ringaskiddy (IE)

( * ) Notice: Subject to any disclaimer, the term of this patent is extended or adjusted under 35 U.S.C. 154(b) by 473 days.

(21) Appl. No.: 18/122,972

(22) Filed: Mar. 17, 2023

(65) Prior Publication Data

US 2024/0312141 A1 Sep. 19, 2024

(51) Int. Cl.
*G06T 19/00* (2011.01)
*A61B 34/00* (2016.01)
(Continued)

(52) U.S. Cl.
CPC ............ *G06T 19/006* (2013.01); *A61B 34/10* (2016.02); *A61B 34/20* (2016.02); *A61B 34/25* (2016.02);
(Continued)

(58) Field of Classification Search
None
See application file for complete search history.

(56) References Cited

U.S. PATENT DOCUMENTS 10,278,778 B2 * 5/2019 State ...................... A61B 34/20
2016/0287337 A1 10/2016 Aram et al.
(Continued)

FOREIGN PATENT DOCUMENTS

WO 2010102197 A2 9/2010
WO 2020214645 A1 10/2020
WO 2021007418 A2 1/2021
WO 2021011760 A1 1/2021
WO 2021163039 A1 8/2021

OTHER PUBLICATIONS

Brainlab, "Knee 3 Surgical Technique", Brainlab.com, 2015, 58 pages.

(Continued)

*Primary Examiner* — Michael J Cobb
(74) *Attorney, Agent, or Firm* — Condo Roccia Koptiw LLP

(57) ABSTRACT

Systems and methods are disclosed for computer aided surgery (CAS), comprising an augmented reality (AR) system configured to display augmented reality information, a position tracking system configured to track positions of objects, an instrument coupled to a tracker detectable by the position tracking system, and a controller configured to: display augmented reality information comprising an indicator of a cut on the bone that would be produced by a current orientation of the instrument and an indicator of a predetermined target plane for the cut, determine, as the instrument is moved, when the current orientation of the instrument is aligned with the predetermined target plane, and based on the determined alignment, display augmented reality information comprising an indicator representing that the current orientation of the instrument is aligned with the predetermined target plane. In some embodiments, the controller is further configured to display augmented reality information comprising an indicator of the axis of the bone.

20 Claims, 6 Drawing Sheets

(51) Int. Cl.
*A61B 34/10* (2016.01)
*A61B 34/20* (2016.01)
*G06V 10/74* (2022.01)

(52) U.S. Cl.
CPC .... *G06V 10/761* (2022.01); *A61B 2034/2065* (2016.02)

(56) References Cited

U.S. PATENT DOCUMENTS

| | | | | |
|---|---|---|---|---|
| 2017/0312032 | A1* | 11/2017 | Amanatullah | G09B 23/30 |
| 2018/0256256 | A1* | 9/2018 | May | A61B 34/10 |
| 2018/0325610 | A1 | 11/2018 | Cameron et al. | |
| 2019/0053855 | A1 | 2/2019 | Siemionow et al. | |
| 2020/0085511 | A1 | 3/2020 | Oezbek et al. | |
| 2021/0065911 | A1* | 3/2021 | Goel | G16H 50/20 |
| 2021/0106386 | A1 | 4/2021 | Lang | |
| 2021/0353311 | A1* | 11/2021 | Lavallee | A61B 17/1675 |
| 2021/0378752 | A1 | 12/2021 | Paul et al. | |
| 2022/0079675 | A1 | 3/2022 | Lang | |
| 2024/0282221 | A1* | 8/2024 | Perler | A61B 34/10 |

OTHER PUBLICATIONS

Spine Navigation Clinical Workflow, https://www.brainlab.com/video-plaverigRIL88A/, Jan. 19, 2021.

Medtronic Navigation, Inc., "StealthStation S7 Treatment Guidance System Manual", A Guide to Understanding the StealthStation S7 Treatment Guidance System, Part No. 9733782, revision 14, Apr. 2012, 74 pages.

Patil, Arun A, "A Modified Stereotactic Frame as an Instrument Holder for Frameless Stereotaxis: Technical Note", Surgical Neurology International, http://www.surgicalneurologyint.com/text.asp?2010/1/1/62/70957, Oct. 2010, 5 pages.

Qian, et al., "ARssist: Augmented Reality on a Head-Mounted Display for the First Assistant in Robotic Surgery", Healthcare Technology Letters, vol. 5, No. 5, 2018, pp. 194-200.

Smith & Nephew, "RI. Hip Navigation Total Hip Arthroplasty, Surgical Technique—Lateral Position", 28 pages.

* cited by examiner

AUGMENTED REALITY (AR) VIRTUAL OBJECTS FOR ALIGNING AN INSTRUMENT PLANE WITH A PLANNED TARGET PLANE

BACKGROUND

Many surgical procedures require large amounts of information for planning and/or undertaking the procedure. One way to manage this is to improve the way information is presented to a user, e.g., a surgeon. Augmented Reality (AR) provides an overlay of virtual information on or adjacent to a "real-world" object visually perceived by a user, usually through an AR device such as a headset, GOOGLE GLASS™ AR device, etc. An AR device is configured to display information, such as pictures, video, text, warnings, models, simulations, etc., while not obscuring the user's view of the real-world objects in her proximity.

However, the information displayed may be selectable, pertinent, and customizable. For example, it would be beneficial to provide information that helps a surgeon visualize items that can't be directly perceived. Furthermore, specific use cases may present challenges that can be at least ameliorated by properly configured AR systems.

Accordingly, there is a need for improved systems, methods, and devices to employ AR that can improve patient outcome and surgical efficiency.

SUMMARY

Systems and methods are disclosed for computer aided surgery (CAS), comprising an augmented reality (AR) system configured to display augmented reality information, a position tracking system configured to track positions of objects, an instrument coupled to a tracker detectable by the position tracking system, and a controller configured to: display augmented reality information comprising an indicator of a cut on the bone that would be produced by a current orientation of the instrument and an indicator of a predetermined target plane for the cut, determine, as the instrument is moved, when the current orientation of the instrument is aligned with the predetermined target plane, and based on the determined alignment, display augmented reality information comprising an indicator representing that the current orientation of the instrument is aligned with the predetermined target plane. In some embodiments, the controller is further configured to display augmented reality information comprising an indicator of the axis of the bone. In some embodiments, the predetermined target plane is defined from acquired bony landmark points, such as in an image-less planning procedure.

DETAILED DESCRIPTION

Figure 1:
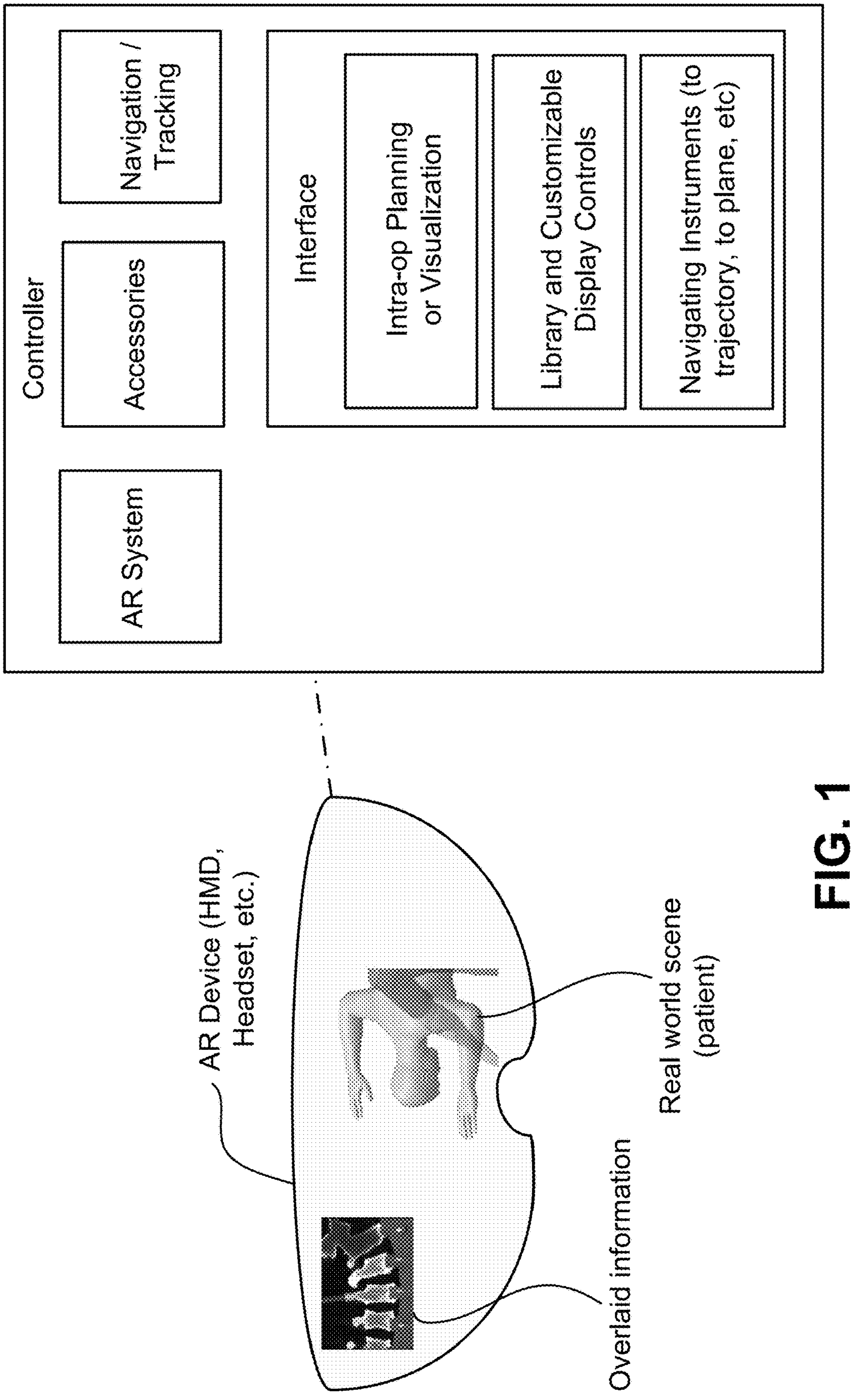
FIG. 1 depicts a computer aided surgery (CAS) system employing Augmented Reality (AR).

FIG. 1 depicts a computer aided surgery (CAS) system employing Augmented Reality (AR). A user (e.g., surgeon) views a patient or other real-world object (instruments, operating room (OR) features, etc.) while receiving an overlay of virtual information from the controller. The information may be stored information or streamed information. Examples of information include pictures, video, text, warnings, models, simulations, etc. The information displayed may be selectable, pertinent, and customizable. For example, intra-op planning may greatly benefit from AR systems, provided it does not negatively impact workflow. Furthermore, specific use cases, such as position-finding of instruments relative to a patient, may present challenges that may be at least ameliorated by properly configured AR systems.

Methods and implementations are provided to assist a surgeon to perform intra-operative (intra-op) visualization and/or planning from an AR headset, with minimal impact to their workflow. AR provides control to the surgeon, for example, for orthopedic procedures. Example applications include knee surgery (e.g., total knee arthroplasty (TKA) or uni-compartmental knee arthroplasty (UKA)), and other orthopedic surgeries. In some embodiments, the system may enhance what the surgeon may see and help the surgeon visualize what they can't see. The display may include virtual targets on the anatomy and information related to the instrument relative to the target. Provided is an AR system that has a user interface (e.g., with a controller) and a display, such as is typically associated with a headset, head-mounted display (HMD), GOOGLE GLASS™ AR device, etc. As will be described, navigation/tracking may be provided. In some embodiments, this application is directed to computer aided surgery (CAS) comprising an augmented reality (AR) system configured to display augmented reality information, a position tracking system configured to track positions of objects, an instrument coupled to a navigational tracker detectable by the position tracking system, and a controller configured to determine a position of the instrument, based on the determined position, display augmented reality information using the AR system. The controller may be used to send and receive information to and from the AR system. The controller typically includes a power supply, AC/DC converters, control system interface circuits, and other components included in computer aided surgery. The controller is also configured to perform the systems and methods described herein.

The controller may be configured for navigation and/or tracking. A position tracking system may comprise a tracker comprising a navigation array including a plurality of markers in a unique constellation or geometric arrangement. For example, optical navigation or tracking systems may utilize stereoscopic sensors (of a tracking unit) to detect light emitting diodes (LEDs) or infra-red (IR) light reflected or emitted from one or more optical markers affixed to the array. For example, when the markers are reflective elements, once detected by stereoscopic sensors, the relative arrangement of the elements in the sensors' field of view, in combination with the known geometric arrangement of the elements, may allow the system to determine a three-dimensional position of the array, and hence the instrument. Other examples of tracking systems in include ultrasonic sensors, radio-frequency identification (RFID) sensors or other radio frequency (RF) tracking systems, electromagnetic interference (EMI) tracking systems, etc. The tracking unit may detect the relative motions between any and all trackers in real time. The tracking unit (e.g., a stereoscopic reflector detecting camera, an AR system camera, or a stand-alone camera) may track the trackers for purposes of determining their relative locations and orientations (e.g., position). A surgeon may view the patient through the AR system and may manipulate the instrument. In some embodiments, a computer aided surgery (CAS) system may comprise an augmented reality (AR) system configured to display augmented reality information, a position tracking system configured to track positions of objects, an instrument coupled to a tracker detectable by the position tracking system, and a controller. The controller may be configured to cause the AR system to display, such as on the headset, augmented reality information about a position of the instrument and a position of the patient. Other augmented reality information may be overlaid (e.g., displayed on the headset as superimposed on the real-world scene). The controller may be configured to, if the instrument moves to another position, cause the AR system to display updated augmented reality information, as will now be described in greater detail. As can be appreciated, using a two-dimensional display to guide a surgeon trying to manipulate or adjust an instrument in three dimensions can be an imposing challenge.

Figure 2:
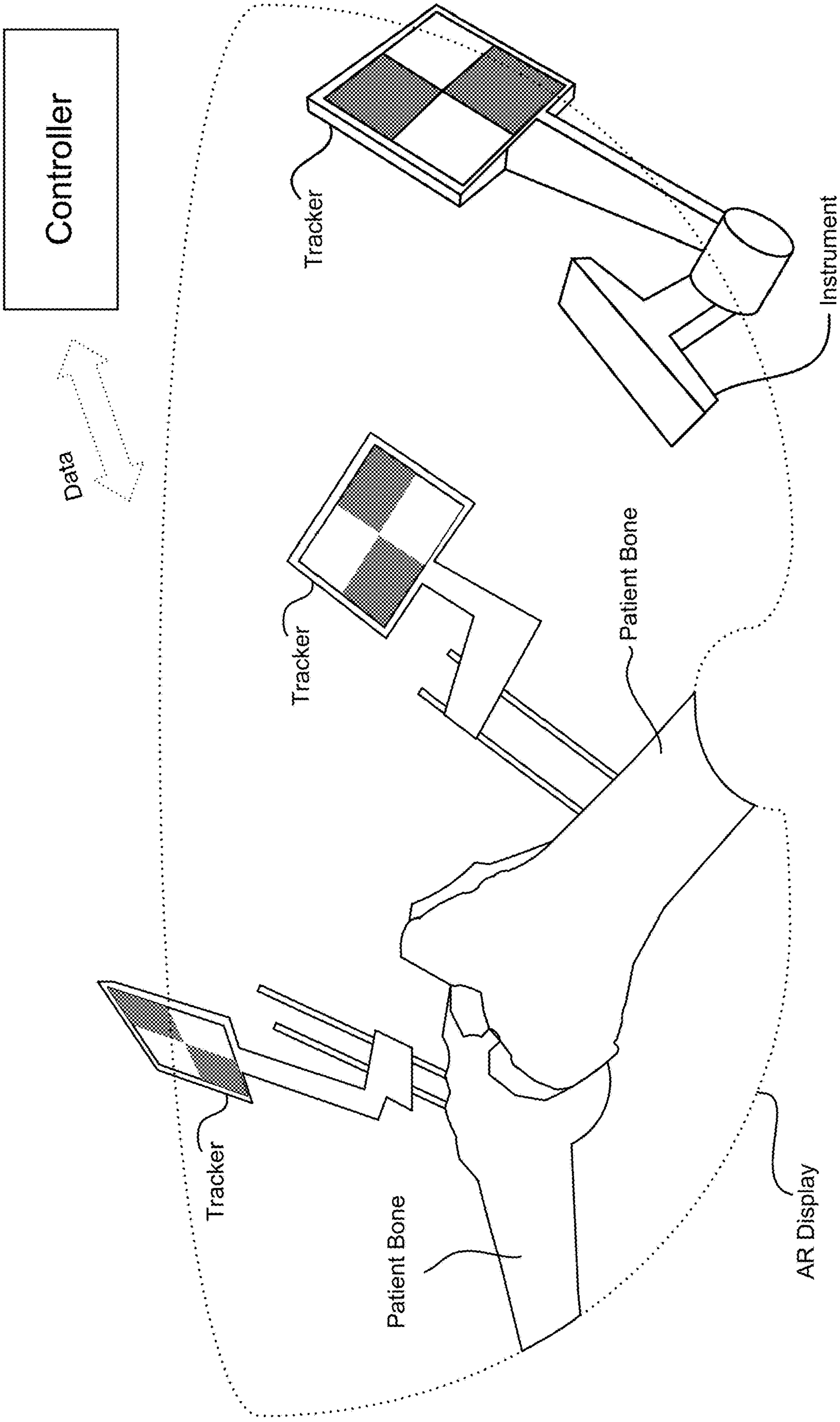
FIG. 2 depicts another embodiment of the computer aided surgery (CAS) system.

FIG. 2 depicts another embodiment of the computer aided surgery (CAS) system. In this embodiment, the tracker is one that is detectable by a camera of the headset (AR system), or alternatively by a separate camera mounted to the headset, or alternatively by a camera separate and located remotely from the headset. For example, the tracker may be a chest type tracker (e.g., having one or more markers used for camera pose estimation) as depicted. Other trackers, such as an ArUco-type tracker or reflective optical markers are also contemplated. The tracker may reveal a position of the instrument (e.g., the tracker may help provide complete positioning information of the instrument which may be used by the controller). The camera may capture a position of the tracker. The relative pose or three-dimensional position (e.g., location and orientation) of the tracker may be tracked and shared with the controller. This information may thus identify a position (e.g., location and orientation) of the instrument to which the tracker is coupled in three-dimensional space given the known and precise relationship between the tracker and the instrument. For example, the controller may be configured to identify a 3D position of a portion of the instrument.

One or more trackers may be attached to a patient, and another tracker attached to the instrument, thus allowing the position of the instrument to be relative to the patient. The controller may determine (or be informed of) a position of a patient anatomy (a femur, a tibia, etc.). The additional tracker(s) may be present elsewhere in an operating theater, e.g., such as coupled to a surgical table. The additional tracker(s) may assist with tracking an anatomy (e.g., a bone) of interest. A patient coordinate system may be defined to refer to the position of the patient with respect to the instrument.

The camera (e.g., an AR system camera or a stand-alone camera) may track the trackers for purposes of determining their relative locations and orientations (e.g., position) and, in some cases, for displaying virtual information as will be described. A surgeon may view the patient through the AR system and may manipulate the instrument. In some embodiments, a computer aided surgery (CAS) system may comprise an augmented reality (AR) system configured to display augmented reality information, a position tracking system configured to track positions of objects, an instrument coupled to a tracker detectable by the position tracking system, and a controller. The controller may be configured to cause the AR system to display, such as on the headset, augmented reality information about a position of the instrument and a position of the patient. The controller may be configured to, if the instrument moves to another position, cause the AR system to display updated augmented reality information, as will now be described in greater detail.

Figures 3A, 3B, 3C:
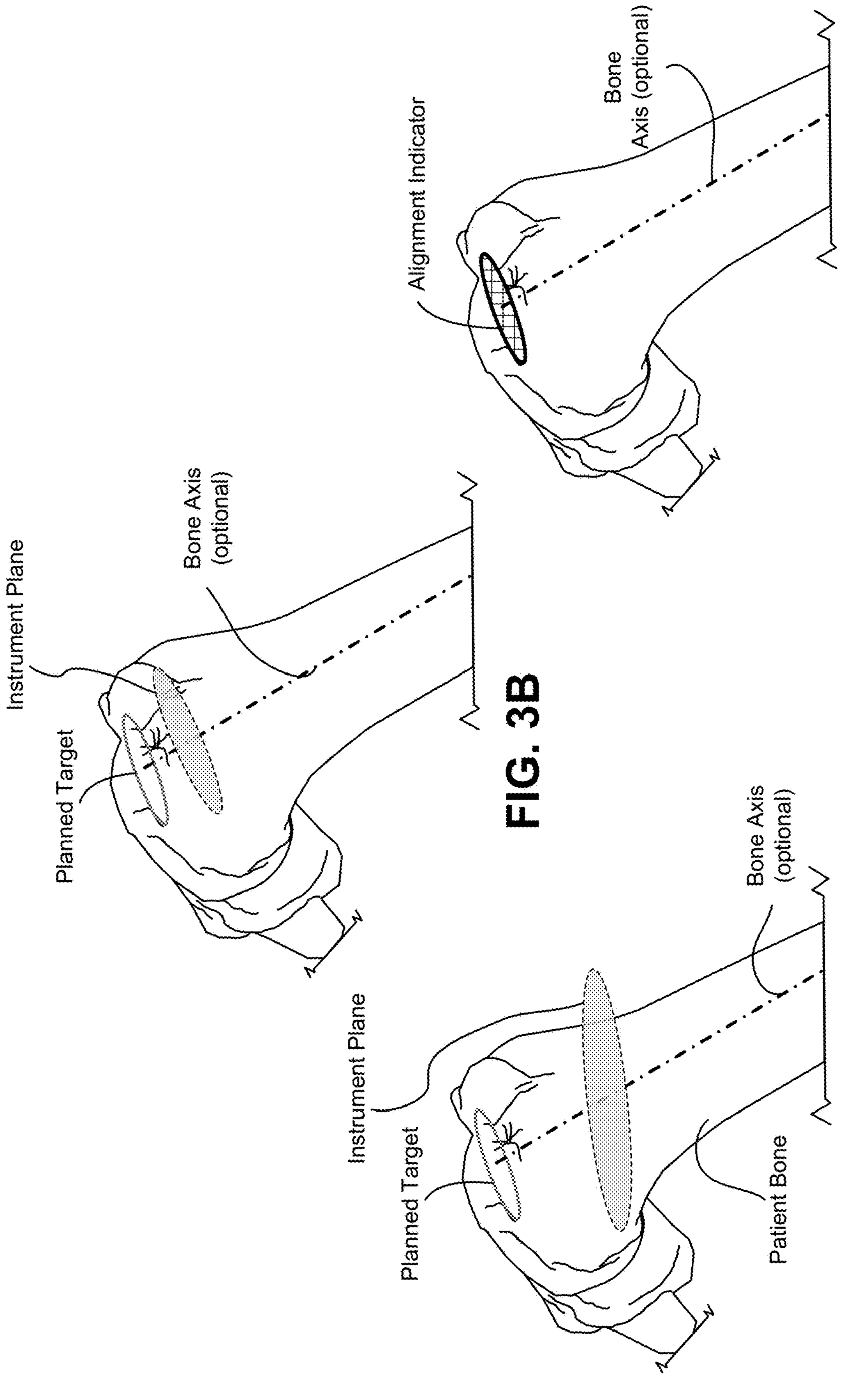
FIGS. 3A-C depict a schematic of views displayed on an AR display having virtual indicators overlaid over a real world scene, the indicators including an optional bone axis, a current orientation of an instrument, a predetermined (e.g., planned) target plane for the instrument, and an alignment indicator (where the instrument is successfully aligned with the plane).

FIGS. 3A-C depict a schematic of views displayed on an AR display having virtual indicators overlaid over a real world scene, the indicators including an optional bone axis, a current orientation of an instrument, a predetermined (e.g., planned) target plane for the instrument, and an alignment indicator (where the instrument is successfully aligned with the plane). The user interface for navigating and aligning an instrument such as a cut guide to a planned cut plane is difficult to make intuitive for users because of the 3D aspect of the task. The AR displays in the following figures provide interfaces that a user may find intuitive for such alignment.

At FIG. 3A, a surgeon may be looking at a patient bone. The bone may be obscured by tissue, and so optionally, an outline of the bone may be displayed elsewhere in the AR display, such as above or next to the patient (FIG. 1). Stated differently, the controller may be configured to display augmented reality information using the AR system, the augmented reality information comprising an outline of the bone or other information. The surgeon may have input the type of procedure into the controller. For example, the procedure may be a so-called "imageless" procedure, where a target plane for a procedure on a bone is planned without using previously acquired three dimensional (3D) images of the bone, for example, such as images taken by a CT, MRI or X-ray system. In such imageless procedures, the surgeon typically does the planning intra-operatively and will obtain information about the bone by touching the exposed bone (after incision) with a tracked pointer (e.g., to acquire points which may define landmarks, the landmarks being used to define a cut plane or target plane). For example, the surgeon may collect information regarding at least three points or landmarks on the bone of the patient. Examples of such landmarks or points include the most medial point on the tibial plateau, the most posterior point on the tibial plateau, the most anterior point on the tibial plateau, the most distal point on the femoral condyle, and the like. Further, the surgeon might collect a cloud of points which can be used to infer landmark points. These points may be used to plan a target plane for the instrument. In the case where the instrument is a cut guide, the predetermined (e.g., planned) target plane for the instrument is equivalent to a predetermined (e.g., planned) target plane for a cut on the bone. The controller may be configured to display augmented reality information using the AR system, the augmented reality information comprising an indicator of the planned target plane. In FIG. 3A, the planned target indicator is an ellipse of a first color displayed on the AR display superimposed on the real-world patient. Optionally, the ellipse may be filled, cross-hatched, etc. Other symmetrical shapes are contemplated for the indicators described herein (circles, disks, polygons, etc.).

Optionally, the controller is further configured to determine an axis of the bone and display augmented reality information comprising an indicator of the axis of the bone. As depicted, the bone axis is a dotted line, but other indicators are contemplated. For example, a surgeon may manipulate a limb of the patient where the bone to be treated is located (e.g., in knee surgery, the surgeon moves the leg and flexes and extends the knee) and the controller (e.g., using the tracking system) may determine the axis. The optional bone axis indicator may be beneficial to the surgeon, for example in cases where the instrument plane should be perpendicular to the bone axis. Preferably, the indicator of the axis of the bone is displayed for at least a portion of the surgical planning procedure. The controller may be configured to toggle display of the bone axis indicator on or off upon an input from the user.

Continuing with the example where the instrument is a cut guide, the controller is further configured to determine a cut on the bone that would be produced by a current orientation of the instrument. Moreover, the controller is further configured to display augmented reality information using the AR system, the augmented reality information comprising an indicator of a cut on the bone that would be produced by a current orientation of the instrument. In FIG. 3A, the instrument plane is an ellipse of a second color displayed on the AR display superimposed on the real-world patient. In some embodiments, the instrument plane ellipse is filled or cross-hatched and/or has a different line type from the planned target ellipse (e.g., in addition to color difference).

Turning to FIG. 3B, the surgeon moves the instrument, attempting to align the instrument plane ellipse with the planned target ellipse. The instrument plane ellipse is an indicator of the cut on the bone that would be produced by the current orientation of the instrument. As can be seen, the controller is further configured to display the instrument plane ellipse as decreasing in size as the current orientation of the instrument is brought closer to alignment with the predetermined target plane. It is understood that controller is further configured to display the instrument plane ellipse as increasing in size if the current orientation of the instrument gets farther from alignment with the predetermined target plane. Optionally, the ellipse shape may change to indicate instrument angle.

Turning to FIG. 3C, the surgeon has moved the instrument so that the current orientation of the instrument is aligned with the predetermined target plane. The controller may determine alignment (e.g., with a precision sufficient for the procedure). Based on the determined alignment, the controller may be further configured to display augmented reality information comprising an indicator representing that the current orientation of the instrument is aligned with the predetermined target plane. The alignment indicator is an ellipse of a third color displayed on the AR display superimposed on the real-world patient. In some embodiments, the alignment indicator replaces the planned target indicator. In some embodiments, the alignment indicator is filled or cross-hatched and/or has a different line type from the planned target indicator (e.g., in addition to color difference) . In some embodiments, the alignment indicator is in a different location. In some embodiments, the alignment indicator is superimposed on another indicator (for example, a flashing planned target indicator, a check mark on top of the planned target indicator, a ring drawn around planned target indicator, etc.).

Figure 4A:
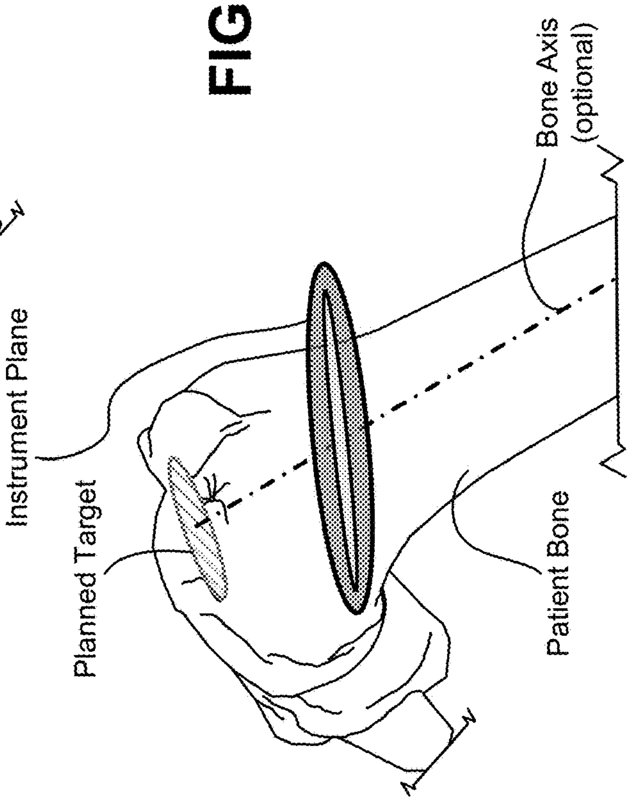
FIGS. 4A-C depict a schematic of views displayed on an AR display according to another embodiment.
Figure 4B:
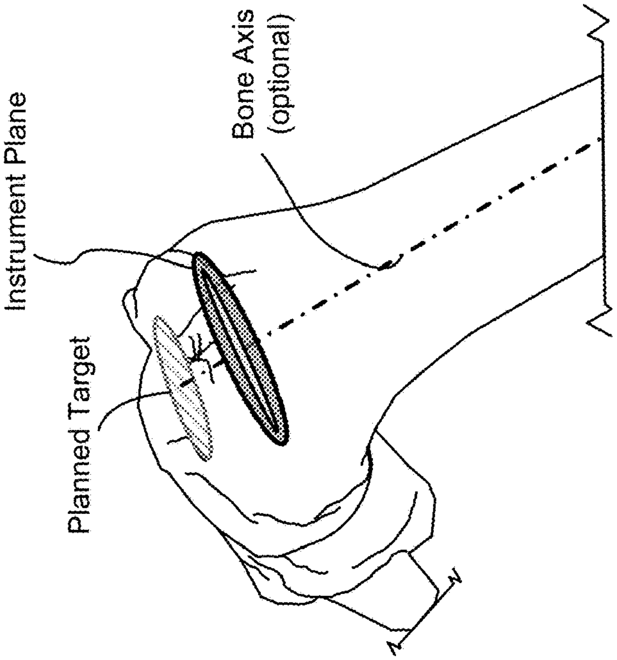
Figure 4C:
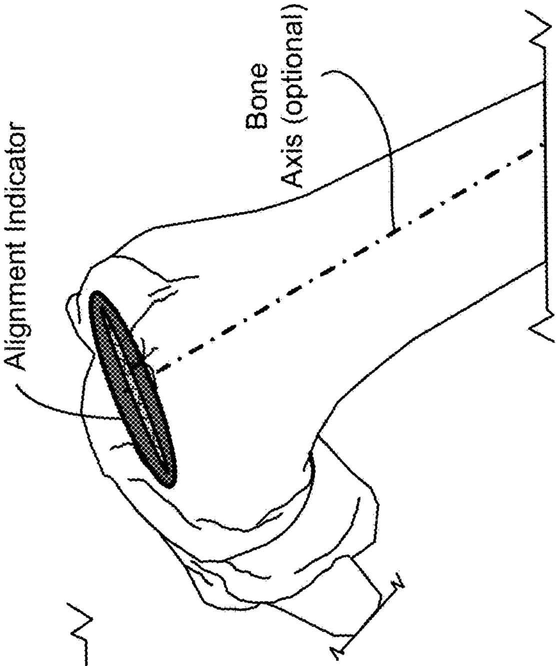

FIGS. 4A-C depict a schematic of views displayed on an AR display according to another embodiment, having virtual indicators overlaid over a real world scene, the indicators including an optional bone axis, a current orientation of an instrument, a predetermined (e.g., planned) target plane for the instrument, and an alignment indicator (where the instrument is successfully aligned with the plane). It will be understood that the surgical planning and use aspects are substantially similar to that previously described with respect to FIGS. 3A-C, and so this description focuses on the virtual indicators displayed on the AR system.

At FIG. 4A, a surgeon may be looking at a patient bone, and the controller may be configured to display augmented reality information using the AR system, the augmented reality information comprising an indicator of the planned target plane. In FIG. 4A, the planned target indicator is an ellipse of a first color displayed on the AR display superimposed on the real-world patient. Optionally, the ellipse may be filled, cross-hatched, etc. Other symmetrical shapes are contemplated for the indicators described herein (circles, disks, polygons, etc.).

The controller is further configured to display augmented reality information using the AR system, the augmented reality information comprising an indicator of a cut on the bone that would be produced by a current orientation of the instrument. In FIG. 4A, the instrument plane indicator is an ellipse with annular border, which may help a surgeon visualize the 3D nature of the plane and assist in alignment. The instrument plane indicator may be displayed as a second color displayed on the AR display superimposed on the real-world patient. In some embodiments, the instrument plane ellipse is filled or cross-hatched and/or has a different line type from the planned target ellipse (e.g., in addition to color difference). The optional bone axis indicator may be beneficial to the surgeon, for example in cases where the instrument plane should be perpendicular to the bone axis. The controller may be configured to toggle display of the bone axis indicator on or off upon an input from the user.

Turning to FIG. 4B, the surgeon moves the instrument, and the controller is further configured to display the instrument plane ellipse as decreasing in size as the current orientation of the instrument is brought closer to alignment with the predetermined target plane.

Turning to FIG. 4C, the surgeon has moved the instrument so that the current orientation of the instrument is aligned with the predetermined target plane (e.g., with a precision sufficient for the procedure). Based on the determined alignment, the controller may be further configured to display augmented reality information comprising an indicator representing that the current orientation of the instrument is aligned with the predetermined target plane. The alignment indicator is an ellipse of a third color displayed on the AR display superimposed on the real-world patient. In some embodiments, the alignment indicator replaces the planned target indicator. In some embodiments, the alignment indicator is filled or cross-hatched and/or has a different line type from the planned target indicator (e.g., in addition to color difference). In some embodiments, the alignment indicator is in a different location. In some embodiments, the alignment indicator is superimposed on another indicator (for example, a flashing planned target indicator, a check mark on top of the planned target indicator, a ring drawn around planned target indicator, etc.).

Figure 5A:
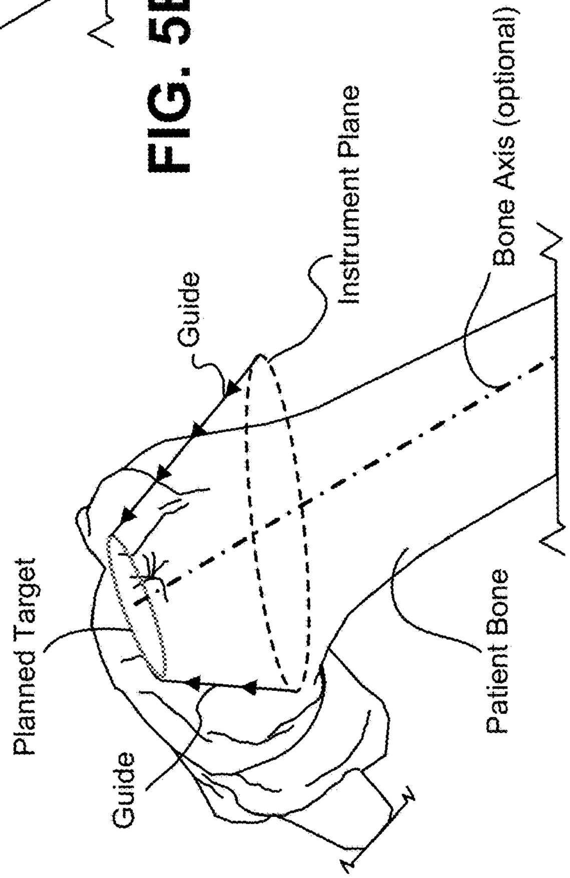
FIGS. 5A-C depict a schematic of views displayed on an AR display according to another embodiment, further comprising additional alignment virtual indicators.
Figure 5B:
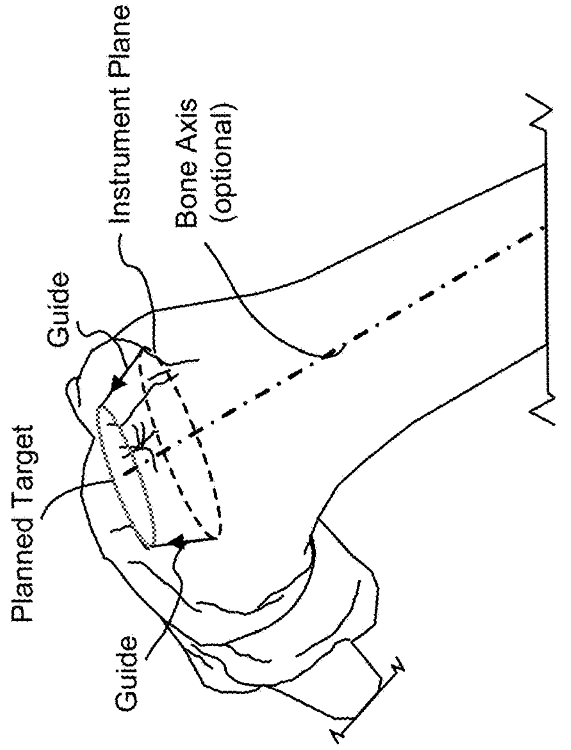
Figure 5C:
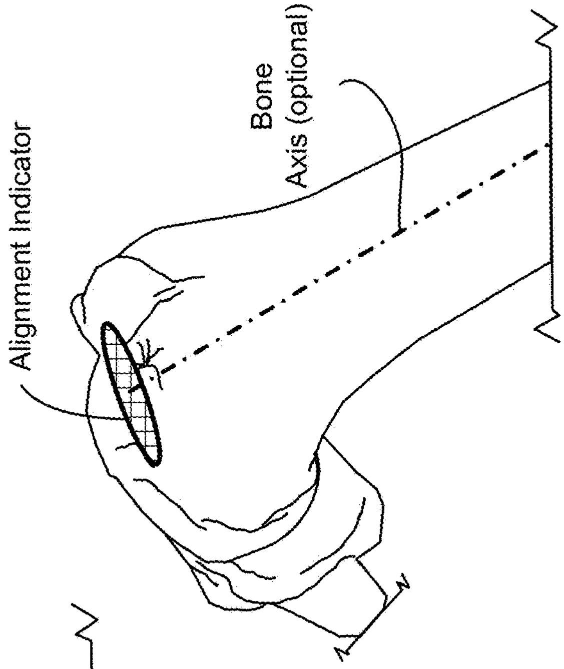

FIGS. 5A-C depict a schematic of views displayed on an AR display according to another embodiment, having virtual indicators overlaid over a real world scene, the indicators including an optional bone axis, a current orientation of an instrument, a predetermined (e.g., planned) target plane for the instrument, an alignment indicator (where the instrument is successfully aligned with the plane), and further comprising additional alignment virtual indicators. It will be understood that the surgical planning and use aspects are substantially similar to that previously described with respect to FIGS. 3A-C, and so this description focuses on the virtual indicators displayed on the AR system.

At FIG. 5A, a surgeon may be looking at a patient bone, and the controller may be configured to display augmented reality information using the AR system, the augmented reality information comprising an indicator of the planned target plane. In FIG. 5A, the planned target indicator is an ellipse of a first color displayed on the AR display superimposed on the real-world patient. Optionally, the ellipse may be filled, cross-hatched, etc. Other symmetrical shapes are contemplated for the indicators described herein (circles, disks, polygons, etc.).

The controller is further configured to display augmented reality information using the AR system, the augmented reality information comprising an indicator of a cut on the bone that would be produced by a current orientation of the instrument. In FIG. 5A, the instrument plane indicator is an ellipse of a second color displayed on the AR display superimposed on the real-world patient. In some embodiments, the instrument plane ellipse is filled or cross-hatched and/or has a different line type from the planned target ellipse (e.g., in addition to color difference). The optional bone axis indicator may be beneficial to the surgeon, for example in cases where the instrument plane should be perpendicular to the bone axis. The controller may be configured to toggle display of the bone axis indicator on or off upon an input from the user.

The controller may be further configured to display augmented reality information comprising a guide indicator that is a pair of lines extending between the indicator of the cut on the bone that would be produced by the current orientation of the instrument and the indicator of the predetermined target plane for the cut. The guide indicator may enhance perception of both an angular difference and the magnitude of difference between the current orientation of the instrument and the predetermined target plane. For example, a length of each line may represent a relative difference. The guide indicator may graphically represent a distance between the current orientation of the instrument and the predetermined target plane. For example, each arrow may be a certain preset length such as 1 mm, 5 mm, etc.

Turning to FIG. 5B, the surgeon moves the instrument, and the controller is further configured to display the instrument plane ellipse as decreasing in size as the current orientation of the instrument is brought closer to alignment with the predetermined target plane. Moreover, the guide indicator is displayed as decreasing in size as the current orientation of the instrument is brought closer to alignment with the predetermined target plane.

Turning to FIG. 5C, the surgeon has moved the instrument so that the current orientation of the instrument is aligned with the predetermined target plane (e.g., with a precision sufficient for the procedure). Based on the determined alignment, the controller may be further configured to display augmented reality information comprising an indicator representing that the current orientation of the instrument is aligned with the predetermined target plane. The alignment indicator is an ellipse of a third color displayed on the AR display superimposed on the real-world patient. In some embodiments, the alignment indicator replaces the planned target indicator. In some embodiments, the alignment indicator is filled or cross-hatched and/or has a different line type from the planned target indicator (e.g., in addition to color difference). In some embodiments, the alignment indicator is in a different location. In some embodiments, the alignment indicator is superimposed on another indicator (for example, a flashing planned target indicator, a check mark on top of the planned target indicator, a ring drawn around planned target indicator, etc.). The guide indicator has disappeared (because the instrument plane ellipse is now the same as the planned target ellipse).

Figure 6A:
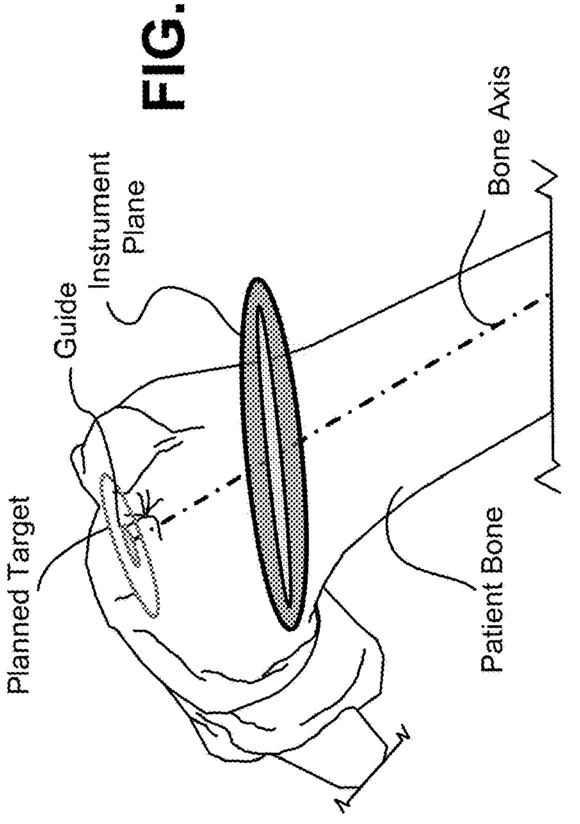
FIGS. 6A-C depict a schematic of views displayed on an AR display according to another embodiment, further comprising an additional alignment virtual indicator according to yet another embodiment.
Figure 6B:
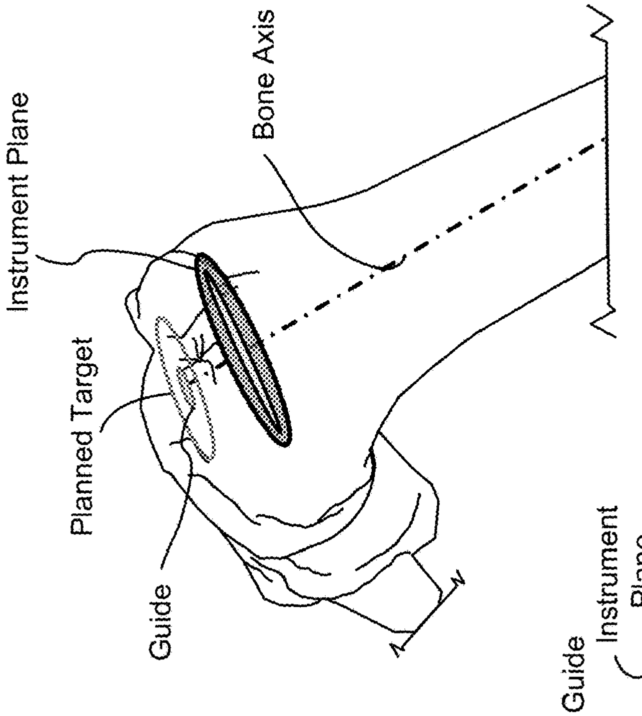
Figure 6C:
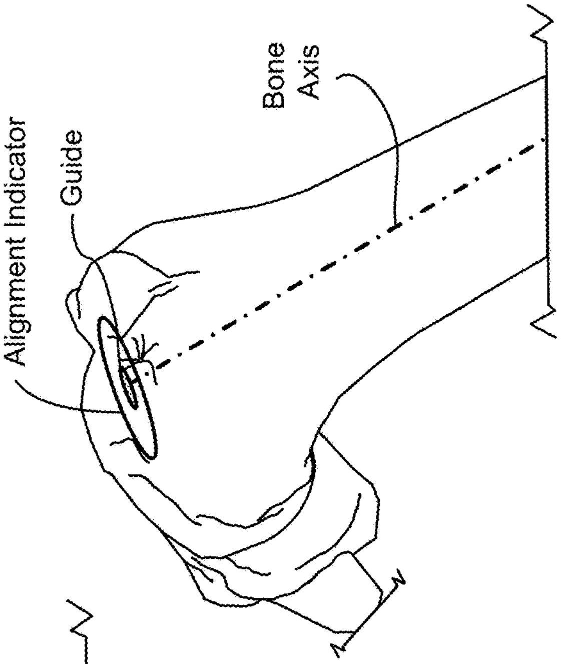

FIGS. 6A-C depict a schematic of views displayed on an AR display according to another embodiment, having virtual indicators overlaid over a real world scene, the indicators including an optional bone axis, a current orientation of an instrument, a predetermined (e.g., planned) target plane for the instrument, an alignment indicator (where the instrument is successfully aligned with the plane), and further comprising an additional alignment virtual indicator according to yet another embodiment. It will be understood that the surgical planning and use aspects are substantially similar to that previously described with respect to FIGS. 3A-C, and so this description focuses on the virtual indicators displayed on the AR system.

At FIG. 6A, a surgeon may be looking at a patient bone, and the controller may be configured to display augmented reality information using the AR system, the augmented reality information comprising an indicator of the planned target plane. In FIG. 6A, the planned target indicator is an ellipse of a first color displayed on the AR display superimposed on the real-world patient. Optionally, the ellipse may be filled, cross-hatched, etc. Other symmetrical shapes are contemplated for the indicators described herein (circles, disks, polygons, etc.).

The controller is further configured to display augmented reality information using the AR system, the augmented reality information comprising an indicator of a cut on the bone that would be produced by a current orientation of the instrument. In FIG. 6A, the instrument plane indicator is an ellipse with annular border, which may help a surgeon visualize the 3D nature of the plane and assist in alignment. The instrument plane indicator may be displayed as a second color displayed on the AR display superimposed on the real-world patient. In some embodiments, the instrument plane ellipse is filled or cross-hatched and/or has a different line type from the planned target ellipse (e.g., in addition to color difference).

The bone axis indicator is displayed in this embodiment. The controller may be further configured to display augmented reality information comprising a guide indicator that is an ellipse centered on an intersection of the axis and the predetermined target plane. The guide indicator may enhance perception of a center of the predetermined target plane.

Turning to FIG. 6B, the surgeon moves the instrument, and the controller is further configured to display the instrument plane ellipse as decreasing in size as the current orientation of the instrument is brought closer to alignment with the predetermined target plane.

Turning to FIG. 6C, the surgeon has moved the instrument so that the current orientation of the instrument is aligned with the predetermined target plane (e.g., with a precision sufficient for the procedure). Based on the determined alignment, the controller may be further configured to display augmented reality information comprising an indicator representing that the current orientation of the instrument is aligned with the predetermined target plane. The alignment indicator is an ellipse of a third color displayed on the AR display superimposed on the real-world patient. In some embodiments, the alignment indicator replaces the planned target indicator. In some embodiments, the alignment indicator is filled or cross-hatched and/or has a different line type from the planned target indicator (e.g., in addition to color difference). In some embodiments, the alignment indicator is in a different location. In some embodiments, the alignment indicator is superimposed on another indicator (for example, a flashing planned target indicator, a check mark on top of the planned target indicator, a ring drawn around planned target indicator, etc.). The guide indicator is still displayed, but in some embodiments, at least one feature of its appearance has changed (color, outline, fill, cross-hatch, etc.).

In a first embodiment, a computer aided surgery (CAS) system is provided. The CAS system comprises an augmented reality (AR) system configured to display augmented reality information; a position tracking system configured to track positions of objects; an instrument coupled to a tracker detectable by the position tracking system; and a controller configured to: receive information regarding at least three points on a bone of a patient; display augmented reality information using the AR system, the augmented reality information comprising an indicator of a cut on the bone that would be produced by a current orientation of the instrument and an indicator of a predetermined target plane for the cut; determine, as the instrument is moved, when the current orientation of the instrument is aligned with the predetermined target plane; and based on the determined alignment, display augmented reality information comprising an indicator representing that the current orientation of the instrument is aligned with the predetermined target plane.

In some embodiments, the at least three points on a bone of a patient are based on acquired points. In some embodiments, the at least three points on a bone of a patient are bony landmarks of the bone. In some embodiments, the controller is further configured to determine the target plane for the cut without using any pre-operative three dimensional (3D) images of the bone.

In some embodiments, the controller is further configured to determine an axis of the bone and display augmented reality information comprising an indicator of the axis of the bone.

In some embodiments, the controller is further configured to display each of the indicators as a different color. In some embodiments, the controller is further configured to display each of the indicators as an ellipse. In some embodiments, the controller is further configured to display the indicator of the cut on the bone that would be produced by the current orientation of the instrument as decreasing in size as the current orientation of the instrument is brought closer to alignment with the predetermined target plane.

In some embodiments, the controller is further configured to display augmented reality information comprising a guide indicator that is a pair of lines extending between the indicator of the cut on the bone that would be produced by the current orientation of the instrument and the indicator of the predetermined target plane for the cut. In some embodiments, the guide indicator enhances perception of an angular difference between the current orientation of the instrument and the predetermined target plane. In some embodiments, the guide indicator graphically represents a distance between the current orientation of the instrument and the predetermined target plane.

In another embodiment, a computer aided surgery (CAS) system is provided. The CAS system comprises an augmented reality (AR) system configured to display augmented reality information; a position tracking system configured to track positions of objects; an instrument coupled to a tracker detectable by the position tracking system; and a controller configured to: receive information regarding at least three points on a bone of a patient; wherein the controller is further configured to determine an axis of the bone and display augmented reality information using the AR system, the augmented reality information comprising an indicator of the axis of the bone; display augmented reality information comprising an indicator of a cut on the bone that would be produced by a current orientation of the instrument and an indicator of a predetermined target plane for the cut; determine, as the instrument is moved, when the current orientation of the instrument is aligned with the predetermined target plane; and based on the determined alignment, display augmented reality information comprising an indicator representing that the current orientation of the instrument is aligned with the predetermined target plane.

In some embodiments, the controller is further configured to display augmented reality information comprising a guide indicator that is an ellipse centered on an intersection of the axis and the predetermined target plane.

In some embodiments, the at least three points on a bone of a patient are based on acquired points. In some embodiments, the at least three points on a bone of a patient are bony landmarks of the bone. In some embodiments, the controller is further configured to determine the target plane for the cut without using any pre-operative three dimensional (3D) images of the bone.

In some embodiments, the controller is further configured to determine an axis of the bone and display augmented reality information comprising an indicator of the axis of the bone.

In some embodiments, the controller is further configured to display each of the indicators as a different color. In some embodiments, the controller is further configured to display each of the indicators as an ellipse. In some embodiments, the controller is further configured to display the indicator of the cut on the bone that would be produced by the current orientation of the instrument as decreasing in size as the current orientation of the instrument is brought closer to alignment with the predetermined target plane.

In some embodiments, the controller is further configured to display augmented reality information comprising a guide indicator that is a pair of lines extending between the indicator of the cut on the bone that would be produced by the current orientation of the instrument and the indicator of the predetermined target plane for the cut. In some embodiments, the guide indicator enhances perception of an angular difference between the current orientation of the instrument and the predetermined target plane. In some embodiments, the guide indicator graphically represents a distance between the current orientation of the instrument and the predetermined target plane.

In yet another embodiment, a method of computer aided surgery (CAS) is provided. The method comprising determining a position of an instrument, wherein the instrument is coupled to a navigational tracker detectable by a position tracking system; displaying, on an augmented reality (AR) system, augmented reality information comprising an indicator of a cut on the bone that would be produced by a current orientation of the instrument and an indicator of a predetermined target plane for the cut; determining, as the instrument is moved, when the current orientation of the instrument is aligned with the predetermined target plane; and based on the determined alignment, displaying augmented reality information comprising an indicator representing that the current orientation of the instrument is aligned with the predetermined target plane.

In some embodiments, the method further comprises determining an axis of the bone and displaying augmented reality information comprising an indicator of the axis of the bone.

In some embodiments, the method further comprises displaying augmented reality information comprising a guide indicator that is an ellipse centered on an intersection of the axis and the predetermined target plane.

In some embodiments, the method further comprises displaying the indicator of the cut on the bone that would be produced by the current orientation of the instrument as decreasing in size as the current orientation of the instrument is brought closer to alignment with the predetermined target plane.

The embodiments of the present disclosure described above are intended to be merely examples; numerous variations and modifications within the scope of this disclosure. Accordingly, the disclosure is not to be limited by what has been particularly shown and described. All publications and references cited herein are expressly incorporated by reference in their entirety, except for any definitions, subject matter disclaimers or disavowals, and except to the extent that the incorporated material is inconsistent with the express disclosure herein, in which case the language in this disclosure controls.

The invention claimed is:

1. A computer aided surgery (CAS) system, comprising:
- an augmented reality (AR) system;
- a position tracking system comprising a camera;
- an instrument coupled to a tracker detectable by the position tracking system; and
- a controller configured to:
  - receive information regarding at least three physically acquired points on a bone of a patient;
  - display augmented reality information using the AR system, the augmented reality information comprising:
    - an instrument plane indicator of a cut on the bone that would be produced when guided by a current orientation of the instrument; and
    - a target plane indicator of a predetermined target plane for the cut, wherein the predetermined target plane is defined using the points, wherein the target plane indicator is a single symmetrical shape;
  - determine, as the instrument is moved, when the current orientation of the instrument is aligned with the predetermined target plane; and
  - based on the determined alignment, display updated augmented reality information comprising an alignment indicator representing that the current orientation of the instrument is aligned with the predetermined target plane.

2. The system of claim 1, wherein the controller is further configured to determine an axis of the bone and display further augmented reality information comprising a bone axis indicator of the determined axis of the bone.

3. The system of claim 1, wherein the at least three physical points on the bone of the patient are bony landmarks of the bone.

4. The system of claim 1, wherein the controller is further configured to determine the target plane for the cut without using any pre-operative three dimensional (3D) images of the bone.

5. The system of claim 1, wherein the controller is further configured to display each of the indicators as a different color.

6. The system of claim 1, wherein the controller is further configured to display each of the indicators as an ellipse.

7. The system of claim 1, wherein the controller is further configured to display the instrument plane indicator as decreasing in size as the current orientation of the instrument is brought closer to alignment with the predetermined target plane.

8. The system of claim 1, wherein the controller is further configured to display further augmented reality information comprising a guide indicator that is a pair of lines extending between the instrument plane indicator and the target plane indicator.

9. The system of claim 8, wherein, when the pair of lines of the guide indicator are of unequal lengths, there is an angular difference between the current orientation of the instrument and the predetermined target plane.

10. The system of claim 8, wherein, a length of the pair of lines of the guide indicator is proportional to a distance between the current orientation of the instrument and the predetermined target plane.

11. A computer aided surgery (CAS) system, comprising:
- an augmented reality (AR) system;
- a position tracking system;
- an instrument coupled to a tracker detectable by the position tracking system; and
- a controller configured to:
  - receive information regarding at least three physically acquired points on a bone of a patient;
  - determine an axis of the bone;
  - display augmented reality information using the AR system, the augmented reality information comprising:
    - a bone axis indicator of the determined axis of the bone;
    - an instrument plane indicator of a cut on the bone that would be produced when guided by a current orientation of the instrument; and
    - a target plane indicator of a predetermined target plane for the cut, wherein the predetermined target plane is defined using the points, wherein the target plane indicator is a single symmetrical shape;
  - determine, as the instrument is moved, when the current orientation of the instrument is aligned with the predetermined target plane; and
  - based on the determined alignment, display updated augmented reality information comprising an alignment indicator representing that the current orientation of the instrument is aligned with the predetermined target plane.

12. The system of claim 11, wherein the controller is further configured to display further augmented reality information comprising a guide indicator that is an ellipse centered on an intersection of the axis and the predetermined target plane.

13. The system of claim 11, wherein the controller is further configured to determine the target plane for the cut without using any pre-operative three dimensional (3D) images of the bone.

14. The system of claim 11, wherein the controller is further configured to display each of the instrument plane indicator, the target plane indicator, and the alignment indicator as a different color.

15. The system of claim 11, wherein the controller is further configured to display each of the instrument plane indicator, the target plane indicator, and the alignment indicator as an ellipse.

16. The system of claim 11, wherein the controller is further configured to display the instrument plane indicator as decreasing in size as the current orientation of the instrument is brought closer to alignment with the predetermined target plane.

17. A method of computer aided surgery (CAS), comprising:

determining a position of an instrument coupled to a tracker detectable by a position tracking system;

receiving information regarding at least three physically acquired points on a bone of a patient;

displaying, on an augmented reality (AR) system, augmented reality information comprising a single instrument plane indicator of a cut on a bone of a patient that would be produced when guided by a current orientation of the instrument and a single target plane indicator of a predetermined target plane for the cut, wherein the target plane indicator is a single symmetrical shape;

determining, as the instrument is moved, when the current orientation of the instrument is aligned with the predetermined target plane; and based on the determined alignment, displaying updated augmented reality information comprising an alignment indicator representing that the current orientation of the instrument is aligned with the predetermined target plane.

18. The method of claim 17, further comprising determining an axis of the bone and displaying further augmented reality information comprising a bone axis indicator of the determined axis of the bone.

19. The method of claim 17, further comprising displaying further augmented reality information comprising a guide indicator that is an ellipse centered on an intersection of the axis and the predetermined target plane.

20. The method of claim 17, further comprising displaying the instrument plane indicator as decreasing in size as the current orientation of the instrument is brought closer to alignment with the predetermined target plane.

* * * * *